United States Patent [19]

Halling

[11] Patent Number: 5,550,184

[45] Date of Patent: Aug. 27, 1996

[54] HYDROLYZED SILANE EMULSIONS AND THEIR USE AS SURFACE COATINGS

[75] Inventor: Robert A. Halling, Wilmington, Del.

[73] Assignee: E. I. Du Pont de Nemours & Company, Wilmington, Del.

[21] Appl. No.: 206,779

[22] Filed: Mar. 4, 1994

[51] Int. Cl.$^6$ .................. C08J 3/03; C08J 3/07; C09D 183/06
[52] U.S. Cl. .................. 524/837; 524/858; 106/287.12; 427/387
[58] Field of Search ................ 524/837, 858; 106/287.12; 427/387

[56] References Cited

U.S. PATENT DOCUMENTS

| | | | |
|---|---|---|---|
| 3,012,006 | 12/1961 | Holbrook et al. | 260/46.5 |
| 3,422,131 | 1/1969 | Pittman et al. | 260/448.2 |
| 3,442,664 | 5/1969 | Heine | 106/2 |
| 3,450,738 | 6/1969 | Blochl | 260/448.8 |
| 4,024,306 | 5/1977 | Takamizawa et al. | 427/387 |
| 4,089,882 | 5/1978 | Takamizawa et al. | 260/448.2 |
| 4,525,425 | 6/1985 | Church | 428/428 |
| 4,549,003 | 10/1985 | Lim et al. | 528/42 |
| 4,648,904 | 3/1987 | DePasquale et al. | 106/2 |
| 4,687,707 | 8/1987 | Matsuo et al. | 428/336 |
| 4,689,181 | 8/1987 | Blatch | 260/408 |
| 4,877,654 | 10/1989 | Wilson | 427/387 |
| 4,983,459 | 1/1991 | Franz et al. | 428/410 |
| 4,990,377 | 2/1991 | Wilson | 427/387 |
| 5,011,963 | 4/1991 | Ogawa et al. | 556/485 |
| 5,051,129 | 9/1991 | Cuthbert et al. | 106/2 |
| 5,059,649 | 10/1991 | Maxson et al. | 524/398 |
| 5,124,467 | 6/1992 | Rodgers et al. | 556/427 |
| 5,274,159 | 12/1993 | Pellerite et al. | 556/485 |

OTHER PUBLICATIONS

*Webster's New Collegiate Dictionary*, 1973 pp. 55, 1153.
Alastair W. Stupart, Water Repellant Treatments For Brickwork, Oct., 1993, 809–811,.

*Primary Examiner*—Margaret W. Glass

[57] ABSTRACT

Novel and highly reactive hydrolyzed silane emulsions are achieved by emulsifying a hydrolyzable alkoxysilane (e.g., perfluoroalkylethyltris(2-(2-methoxyethoxy)ethoxy)silane, 2-perfluoroalkylethyltris(2-(2-(2-methoxyethoxy)ethoxy)-ethoxy) silane, 2-Perfluoroalkylethyltris(polyoxyethyleneglycolmonomethylether)silane or the like) in water in the presence of an effective amount of an emulsifier of sufficiently high HLB value (preferably 14 or greater) to simultaneously retain said hydrolyzable alkoxysilane compound in a substantially totally hydrolyzed state and inhibit said resulting hydrolyzed alkoxysilane compound from self-condensation. Such reactive emulsions containing fluorocarbon silanes are useful to produce durable coatings that impart oil and water repellency to substrates having siliceous, cellulosic or proteinaceous surfaces.

10 Claims, No Drawings

HYDROLYZED SILANE EMULSIONS AND THEIR USE AS SURFACE COATINGS

BACKGROUND OF THE INVENTION

1. Field of the Invention

The present invention relates to stable hydrolyzed silane aqueous emulsions and their application to various substrates to impart oil and water repellency. More specifically but not by way of limitation, the present invention relates to aqueous emulsions of a fluorocarbon silane and an effective amount of an emulsifier having a hydrophile-lipophile balance, HLB, sufficiently high of retain the fluorocarbon silane in a stable aqueous emulsion in substantially a hydrolyzed state.

2. Description of the Related Art

It is known that hydrolyzable silanes can be formulated as aqueous solutions or emulsions that can be applied to various substrates to impart hydrophobic or water repellency properties. However, for these emulsions to achieve long term storage stability they must be buffered to specific pH ranges to inhibit or prevent the hydrolysis of the silanes in the aqueous medium (see for example, U.S. Pat. No. 4,990,377 and U.S. Pat. No. 4,877,654). It is also known that when hydrolyzable fluorocarbon silanes are applied to various surfaces, they can impart both water repellency and oil repellency to those substrates. However, those hydrolyzable fluorocarbon silanes are applied to the surfaces in the molten state or when dissolved in volatile organic solvents, and must generally be cured by heating with a catalyst to chemically affix the fluorocarbon silane to the substrates (see, U.S. Pat. No. 3,012,006). The use of such volatile solvents are generally harmful to the environment and may be hazardous due to their flammability. Where aqueous solutions or emulsions of the hydrolyzable fluorocarbon silanes are possible, the formulations cannot be stored for long periods of time, especially under a broad range of pH conditions, without undergoing hydrolysis and self-condensation to form insoluble polymeric structures.

It is generally recognized (see, Silane Coupling Agents, E. P Plueddemann, 2 nd. Edition, Plenum Press, NY, 1991; and Silanes And Surfaces, D. E. Leyton, Gordon and Breach Science Publ., NY, 1986) that an important aspect of the durable oil and water repellency that is imparted to surfaces by hydrolyzable fluorocarbon silanes, such as with fluorocarbon alkoxysilanes, is the chemical bonding that occurs between the silane and the active hydrogen functional groups on the substrate. This is achieved by initial hydrolysis of the hydrolyzable groups on the silane to silanol groups, which then undergo condensation with the functionality on the substrate. If there is more than one hydrolyzable group on the silane, multiple silane groups will be formed in the hydrolysis and these silanol groups may condense with the functions on the substrate as well as with adjacent silanol groups attached to the surface. The result is a cross-linked and highly durable fluorocarbon siloxane structure on the surface of the substrate. Accordingly, the highest durability would be expected from the silanes with three hydrolyzable groups on the silicon.

SUMMARY OF THE INVENTION

In view of the above and unlike the solvent based hydrolyzable fluorocarbons and the buffered aqueous trialkoxysilane emulsions of the prior art, it has now been discovered that the aqueous fluorocarbon silane emulsions of this invention contain the silane in an essentially completely hydrolyzed state (measured by NMR as explained more fully later) thus ready for instant bonding to the substrate to provide the repellency properties. Notwithstanding this apparent total hydrolysis and thus highly reactive state of the fluorocarbon silane, the unique aqueous emulsions of the instant invention do not permit the hydrolyzed silanes to self-condense to high molecular weight, water insoluble, polysiloxane structures while in this emulsified state. Thus these emulsions are generally stable to long term storage of one year or more, are stable to broad ranges of pH, typically from about 2.5 to about 11.0, are stable to temperatures of 60° C. or greater, and frequently are stable to repeated freezing and thawing conditions without undergoing coagulation and precipitation of the silane.

In the broadest sense the above observed high reactivity of the emulsion, wherein apparently total hydrolysis of the silane compound in the micelle is achieved simultaneously with long term inhibition of the self-condensation reaction, is felt to be a characteristic of the use of any readily emulsifiable alkoxysilane in combination with an effective amount of an emulsifier of very high HLB value. Thus, the present invention provides for novel aqueous emulsions of unique reactivity and stability comprising: (a) a alkoxysilane compound emulsified in water; and (b) an effective amount of an emulsifier of sufficiently high HLB value to simultaneously retain the alkoxysilane compound in a hydrolyzed state and inhibit the hydrolyzed alkoxysilane compound from appreciable self-condensation.

In one specific embodiment of this invention and consistent with the acknowledged prior art recognition that highest durability is associated with the presence of multiple hydrolyzable groups leading to cross-linked siloxane structures upon condensation on a substrate, the present invention further provides for a perfluoroalkyl substituted trialkoxysilane of the following formula be employed:

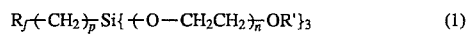  (1)

wherein: $R_f$ is a perfluoroalkyl radical of 3 to 18 carbon atoms; R's are the same or different alkyl radicals of 1 to 3 carbon atoms; and p=2 to 4, and n=2 to 10.

The improved method of using the emulsions for surface coating of a substrate according to the instant invention comprises the steps of:

(a) emulsifying in water (i) a fluorocarbon silane represented by the formula:

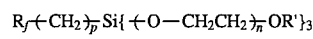

where $R_f$ is a perfluoroalkyl radical of 3 to 18 carbon atoms; R's are the same or different alkyl radicals of 1 to 3 carbon atoms; p=2 to 4; and n=2 to 10 and (ii) an effective amount of an emulsifier of sufficiently high HLB value to simultaneously retain said hydrolyzable alkoxysilane compound in a substantially totally hydrolyzed state and inhibit said hydrolyzed alkoxysilane compound from appreciable self-condensation thus forming a reactive aqueous emulsion; and (b) contacting a substrate with said reactive aqueous emulsion of step (a).

One object of this invention is to produce aqueous emulsions of selected hydrolyzable fluorocarbon silanes that exhibit good stability on storage under a broad range of pH conditions. Another object is to provide such aqueous emulsions wherein the hydrolyzable silane is retained in a highly reactive state by virtue of essentially total hydrolysis of the alkoxy moiety and simultaneously self-condensation is inhibited. Still another object of this invention is to provide an improved process that takes advantage of the highly reactive state of the fluorocarbon silane in the emulsion to render substrates both water repellent and oil repellent by the application of the aqueous emulsions of the hydrolyzed fluorocarbon silanes without the need for special curing operations.

DESCRIPTION OF THE PREFERRED EMBODIMENTS

In describing and exemplifying the various features and aspects of the present invention and in explaining how the present invention differs from and is distinguishable over the previously known compositions and methods of use along with their corresponding advantages, it should be appreciated that the novelty of the present invention should be viewed as being the composite of achieving a highly reactive yet stable aqueous emulsion capable of producing a durable, chemically bonded coating as apposed to the specific properties resulting from the simple coating of the substrate. Even though a specifically preferred embodiment of this invention relates to stable aqueous emulsions of hydrolyzable reactive fluorocarbon silanes that are storage stable and that react with substrate surfaces to impart water and oil repellency, in a broader sense the invention relates generically to any desirable property associated with a silane coating. As such, the following description will utilize the preferred fluorocarbon silanes that encompass essentially all of these features with the understanding that certain features of the invention have much broader implications and as such the specific embodiment should not be interpreted as being unduly limiting.

Aqueous emulsions of the compounds of formula (1), in addition to imparting water and oil repellency to surfaces coated therewith, also impart improved lubricity. This is particularly true of those compounds wherein $R_f$ contains a greater number of carbon atoms, particularly when $R_f$ contains 12–18 carbon atoms. This increased lubricity is of course more readily observed if the substrate coated has a smooth surface. This increased lubricity (i.e., decreased coefficient of friction) renders the surface more scratch resistant.

The fluorocarbon silanes useful in this invention are represented by the following formula:

$$R_f(CH_2)_p Si\{(O-CH_2CH_2)_n OR'\}_3 \quad (1)$$

wherein: $R_f$ is a perfluoroalkyl radical of 3 to 18 carbon atoms; R's are the same or different alkyl radicals of 1 to 3 carbon atoms; p=2 to 4, and n=2 to 10. The preferred compositions are: $R_f$=mixed perfluoroalkyl groups with an average of 8 to 12 carbons; R'= methyl; and p=2; and n=2 to 4.

When n=2, the preferred composition is perfluoroalkylethyltris(2-(2methoxyethoxy)ethoxy)silane. When n=3, the preferred composition is 2-perfluoroalkylethyltris( 2-(2-(2-methoxyethoxy)ethoxy)ethoxy)silane.

The fluorocarbon silanes of this invention are prepared by methods known in the art for hydrocarbon silanes (see, Kirk-Othmer, Encyclopedia of Chemical Technology, third edition, vol. 20, and Mehrota, R. C., Pure Appl. Chem., 13, 111; 1966). The preferred method is by reacting the corresponding perfluoroalkyl trichlorosilane with the proper ether alcohol, such as, diethylene glycol monomethyl ether or triethylene glycol monomethyl ether, for example according to the following equation:

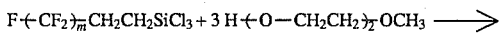

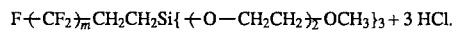

Where m is 6–18.

The fluorinated trichloro silane starting materials for the above reaction can be prepared by one of several recognized procedures: for example see, McBee, E. T., J. Am. Chem. Soc., 79, 2329 (1957); Adv. Organomet. Chem, 17, 407 (1979); U.S. Pat. No. 3,012,006; U.S. Pat. No. 4,089,882 or U.S. Pat. No. 4,549,003. The reaction of perfluoroalkylethylene with trichlorosilane, catalyzed by a platinum complex, is preferred for the preparation of perfluoroalkylethyltrichlorosilane because of the mild reaction conditions and the high yields and purity that are achievable.

The mole ratio of perfluoroalkylethyltrichlorosilane to the ether alcohol employed in the preparation of the silanes for this invention is usually stoichiometric (i.e., 1:3); however, a small excess of the alcohol may be used to force the reaction to completion. The value of m is preferably from 6 to 18 and may be composed of pure components, or more economically, of a mixture of components in this range. A mixture containing a distribution of components with an average m of 8 to 12 is most preferred. The yields from this reaction are essentially quantitative. However, small amounts of oligomers may be produced that do not interfere with the use of the reaction product.

An alternate method, also useful for the preparation of the preferred silanes useful for this invention involves the transesterification of 2-perfluoroalkylethyltrimethoxy (or ethoxy) silane with diethylene glycol monomethyl ether or triethylene glycol monomethylether, with removal of the methanol or ethanol by-products. This reaction usually requires an acid or base catalyst, such as p-toluenesulfonic acid or sodium methoxide, to accelerate the reaction.

Any solvent inert to the reactants and products may be used in the reaction to provide the fluorocarbon silane ether ethoxylates of this invention. If the reactants and products are liquid and mutually miscible under the reaction conditions, the solvent may be omitted. Solvents such as hexane, heptane, toluene and cyclohexane are suitable.

The temperatures suitable for these reactions are those that will effect completion within a reasonable length of time. Temperatures ranging from about 0° C. to 160° C., or to the boiling point of the solvent, may be used. Usually temperatures of from about 25° C. to about 120° C. are employed. Reaction times of from about 2 hours up to 24 hours are usually adequate to complete the reaction.

The reactive hydrolyzable fluorocarbon silanes of the compositions described above possess unique properties that enable them to be formulated into stable aqueous emulsions that impart oil and water repellency to surfaces to which they are applied. The use of volatile organic solvents, which increase costs and may degrade the environment, are not required.

The fluorocarbon silanes suitable for preparation of these aqueous emulsions must possess hydrolyzable groups that impart sufficient hydrophilicity to the silane to permit the initial emulsifiability in the aqueous medium, with or without the emulsifier. In the case of hydrolyzable fluorocarbon silanes represented by formula (1), the preferred compositions have $R_f$ as being mixed perfluoroalkyls with an average of 8 to 12 carbons, R' is a —CH$_3$, p=2 and n=2 to 4. Corresponding compositions with n=0 or 1 will not produce stable aqueous emulsions by this invention. The preferred compositions with n=2 will produce stable aqueous emulsions only in the presence of the emulsifiers of this invention. The preferred composition with n=3 or greater will initially produce aqueous emulsions without the use of the emulsifiers. However, the usable lifetime (i.e., the time that the aqueous emulsion will retain its stability) will be inversely proportional to the concentration of the silane; e.g., from 1–2 hours for a 10% emulsion to 18–24 hours for a 0.5% emulsion. After which time the emulsion becomes hazy and ultimately results in an unusable mixture due to separation of the hydrolyzed and condensed fluorocarbon polysiloxane. However, during this short usable lifetime, the silane emulsion may be applied to a substrate to impart durable oil and water repellency. Thus in general, the highly stable emulsions of the present invention are prepared from silanes of the above formula or the like, such as poly(ether-)alkoxy substituted silanes of sufficient hydrophilicity to achieve .equivalent water emulsifiablity and an appropriately selected emulsifier intimately dispersed in an aqueous mixture.

Emulsifiers usable to prepare the stable aqueous emulsions of the hydrolyzable fluorocarbons silanes of this invention may be chosen from anionic, cationic, nonionic, and amphoteric types. Preferred emulsifiers are those that have an HLB ("The HLB System" published by ICI America's Inc., Wilmington, Del.; Adamson, A. W., "Physical Chemistry of Surfaces", 4th. Ed., John Wily & Sons, N.Y., 1982, p. 475) value greater than 12, and preferably greater than 16. Emulsifiers with HLB values from 12 to 16 may be used, but, usually require significantly greater quantities of the emulsifier to achieve emulsions of adequate stability. Emulsifiers with HLB values below 12 do not form stable emulsions with preferred compositions of this invention. Mixtures of emulsifiers that each meet the above HLB requirements may be used; if they are compatible with one another. Suitable emulsifiers include, but are not limited to, alkylbenzenesulfonates, linear alkyldiphenyletherdisulfonates, alpha-olefin sulfonates, ethoxylated alkyl alcohol ethers, ethoxylated alkyl alcohol ether sulfates, ethoxylated alkylphenols, ethoxylated alkylphenol ether sulfates, ethoxylated perfluoroalkylalkanols, $C_{8-18}$ alkyltrimethylammonium salts, $C_{8-18}$ alkyldimethylammonium salts, ethoxylated $C_{8-18}$ amine salts, alpha-trimethylamino fatty acid betaines and perfluoroalkyl amphoteric surfactants of the type $R_f$—$CH_2CH(OR'')CH_2N(CH_3)_2CH_2CO_2$(inner salt) where R" is H or acetyl, and quaternary salts of the type $R_f$—$CH_2CH_2SCH_2CH(OH)CH_2N(CH_3)_3^+CL^-$.

The aqueous emulsions of this invention are preferably prepared by dissolving the emulsifier in water and then slowly adding the fluorocarbon silane, employing standard agitation techniques. After the materials are thoroughly blended, the emulsions should stand for up to 72 hours, with or without further agitation, to allow them to fully generate the equilibrium stable composition. However in principle, the emulsifier can be added to an already emulsified water/hydrolyzable silane mixture provided that significant irreversible self-condensation has not taken place.

Analysis of the unique aqueous emulsions of this invention by Nuclear Magnetic Resonance spectroscopy indicates that the alkoxysilanes have undergone hydrolysis to produce hydroxysilanes that are believed to posses the structure:

$$R_f(CH_2)_p Si(OH)_3 \qquad (2)$$

and possibly low molecular weigh oligomers thereof. However, unlike trihydroxysilanes in water mixtures without the emulsifier, these silanes do not undergo condensation to produce insoluble polymeric structures, but remain in a stabilized, emulsified state in the aqueous formulation.

The emulsions normally are essentially colorless, completely clear, water formulations. Particle size measurements by light scattering techniques (Coulter N4MD instrument) show particle sizes of from less than 10 nm to about 300 nm, indicative of true microemulsions or emulsions rather than solutions. Most frequently the particle sizes range from less than 10 nm to 100 nm.

The concentration of the emulsifier in the preferred emulsions is critical and varies with the particular emulsifiers and silanes. The optimum concentration for any given emulsifier/silane system is readily determined by routine procedures. In general, for the silanes of the present invention, the emulsifier may be present at concentrations of from 5 to 100, or more, weight percent based on the silane. The preferred concentrations of emulsifier are in the range of about 10 to 50%. The concentration of the silane may be from 0.01% to 50% by weight, based on the total emulsion, preferably from 0.1 to 25 weight percent for practical reasons.

The clear transparent appearance of an emulsion of this invention is indicative of its stability. Poor stability is recognized by precipitation of the silane as a polymeric species due to condensation to form less soluble siloxane structures which separate from the emulsion.

The preferred fluorocarbon silane emulsions of this invention containing an emulsifier are stable for over 6 months when stored at ambient temperatures. Many are stable at elevated temperatures of up to 60° C. for over two months. Many emulsions, particularly when prepared at emulsifier levels of 30% or greater based on silane weight, are stable to alternate freezing and thawing conditions. Additionally, many of the emulsions are stable at pH levels as high as 11 or as low as 3, if the emulsifier is also unaffected by such conditions. The emulsions of this invention may also be diluted to 0.1% or lower without loss of stability.

The aqueous emulsified fluorocarbon silanes of this invention will interact with functional groups on the surface of the substrate to produce a durable coating of the silane that imparts oil and water repellency to those substrates. The fluorocarbon silane repellent treatment compositions are most useful for imparting repellency to substrates having siliceous, cellulosic or proteinaceous surfaces, and to polymer substrates having pendent active hydrogen groups, such as polyesters and polyamides. Typical of treatable substrates are wood, brick, concrete, masonry, stone, glass, ceramic tile, natural and synthetic fibers, fur and leather.

The substrates are rendered repellent by coating the emulsions on the substrate surface and allowing the coated surface to dry. No curing step is required to achieve the durable repellency properties; however, heat may be applied to accelerate the drying process. The treated surface, after drying, may be washed with water to remove residual emulsifier that may effect the apparent water repellency. The resultant product is a substrate having bonded thereto a surface layer of the hydrolyzed/condensed form of the compound of formula (1) and/or (2).

Various additives such as pigments, biocides, uvabsorbers, and antioxidants may also be advantageously included in the emulsions of the present invention. It is also contemplated mixtures of more than a one silane compound may be used in the emulsions.

The following examples are presented to more fully demonstrate and further illustrate various individual aspects and features of the present invention. In doing so, the preferred perfluoroalkyl trialkoxysilanes are intentionally employed as being generally illustrative of the enhanced reactivity of the hydrolyzed emulsion compositions and generally illustrative of the resulting durable coatings of the process using perfluorocarbon silanes while being specifically illustrative of imparting useful and desirable repellency to substrate surfaces. As such the examples are felt to be non-limiting and are meant to illustrate the invention but are not meant to be unduly limiting in any way particularly with respect to ultimate properties and utility of the coated surfaces.

EXAMPLE 1

Preparation of 2-Perfluoroalkylethyltris[2-(2-methoxyethyoxy)ethoxy]silane:

2-Perfluoroalkylethyltrichlorosilane,-205 g, 0.32 mole, was dissolved in heptane and heated to 75° C. 2-(2-Methoxyethoxy)ethanol, 115.3 g, 0.96 mole, was added slowly to this solution. The hydrogen chloride that evolved was absorbed with a caustic scrubber solution. When the addition was complete, the mixture was heated an additional 24 hours at 75°–80° C. The solvent was removed under vacuum, leaving a clear, colorless liquid product.

EXAMPLE 2

Anionic emulsion:

An aqueous emulsion was prepared from the silane of Example 1 by slowly adding 8.0 g of the alkoxysilane to a stirred solution of 2.4 g of the anionic emulsifier, sodium dodecylbenzenesulfonate, in 89.6 g of water. The emulsion was allowed to stand without agitation for 24 hours to achieve an equilibrium composition, after which it had a pH of 3.65 and appeared clear and colorless. Measurement of particle size with a Coulter N4MD Laser Light Scattering instrument showed an average particle size of 14 nm. The emulsion was stable at ambient temperatures and at 60° C. for more than two months. Freezing and thawing did not affect the stability of the emulsion.

EXAMPLE 3

Cationic Emulsion:

8.0 g of the silane of Example 1 was added slowly to a stirred solution of 2.4 g of hexadecyltrimethylammonium chloride in 89.6 g of water. The emulsion was stirred for 30 minutes after the addition was complete and then allowed to stand for 24 hours to achieve the equilibrium composition. The emulsion had a pH of 5.35 and was clear and colorless, and was stable at ambient temperature and at 60° C. for more than two months. The emulsion was frozen and thawed repeatedly without change in appearance or properties. The emulsion particles were found to have an average particle size of 10 nm. This emulsion was analyzed by quantitative NMR spectroscopy and found to be essentially completely hydrolyzed.

EXAMPLE 4

Nonionic Emulsion:

An aqueous emulsion of the silane of Example 1 was prepared by the method of Example 3, using 8.0 g of the silane, 4.0 g of nonylphenol-50 EO, and 88 g of water. The clear, colorless, aqueous emulsion, with an average particle size of 34 nm, was stable at ambient and elevated temperatures for more than two months, and under repeated freezing and thawing conditions.

EXAMPLE 5

Amphoteric Emulsion:

An aqueous emulsion of the silane of Example 1 was prepared by the method of Example 3, using 8.0 g of the silane, 2.4 g of (2-acetoxy-3-perfluoroalkyl) propylcarboxymethyldimethylammonium inner salt ("ZONYL" FSK of DuPont Co.) and 89.6 g water. The clear, light amber emulsion had a pH of 2.65 and was stable for more than two months at 60° C. and under repeated freeze/thaw cycles. The emulsion particles were found to have an average size of 34 nm.

EXAMPLE 6

Preparation of 2-Perfluoroalkylethyltris[2-(2-(2-methoxyethoxy)ethoxy)ethoxy]silane:

2-Perfluoroalkylethyltrichlorosilane, 205 g, 0.32 mole, was dissolved in heptane. Triethylene glycol monomethyl ether, 157.4 g, 0.96 mole, was added slowly. The reaction temperature was raised to 80° C. and held 24 hours. The hydrogen chloride that was evolved was absorbed in a caustic scrubber solution. The solvent was then removed under vacuum leaving a clear, colorless, slightly viscous liquid product.

EXAMPLE 7

Anionic Emulsion:

An aqueous emulsion of the silane of Example 6 was prepared by the procedure of Example 3, using 9.2 g of the silane, 2.4 g of the anionic surfactant, sodium dodecylbenzenesulfonate, in 88.4 g of water. After standing for 24 hours, the emulsion was clear and colorless and was stable for more than 2 months at 60° C.

EXAMPLE 8

Self-Emulsion:

An aqueous emulsion of the silane of Example 6 was prepared by adding 0.58 g of the silane to 99.4 g of water, without any emulsifiers. The silane became emulsified immediately forming a colorless, clear aqueous mixture. After 18 hours the emulsion became hazy, and after 20 hours a gel and a white precipitate formed in the emulsion, indicating that it had lost its stability and condensed to an insoluble polymeric siloxane. Repellency tests presented in Example 9 were run on this emulsion within the first 8 hours after it was prepared, while it was still colorless and clear.

EXAMPLE 9

Repellency Tests:

The emulsions, prepared in Examples 2–8, were diluted with water to a concentration of 0.50 weight % active ingredient (before hydrolysis) and applied to several substrates. The oil and water repellent properties of these substrates were measured using AATCC (American Association of Textile Chemists and Colorists) Method 118-1978 wherein oil and water ratings of 0 indicate no repellency and ratings of 6 indicate the highest level of repellency. The fluorocarbon silanes were applied at the rate of 1 mg of active ingredient per square inch of substrate, and allowed to dry for 24 hours. The test pieces were then soaked in water for 30 minutes and again air dried for 24 hours before being tested for their repellency by the AATCC Method. The results are listed in Table I. The data illustrate the high levels of oil and water repellency imparted by the emulsion of this invention on a variety of substrates.

TABLE I

REPELLENCY PERFORMANCE OF HYDROLYZABLE SILANE EMULSIONS
Oil/Water Repellency Rating

| Example | Wood | Brick | Cement Block | "Formica" Plastic Laminate | Ceramic Tile | Plate Glass |
|---|---|---|---|---|---|---|
| Control | 0/0 | 0/0 | 0/0 | 0/5 | 0/0 | 0/0 |
| 2 | 4/4 | 3/4 | 3/4 | 6/6 | 6/6 | 1/1 |
| 3 | 1/2 | 3/4 | 5/6 | 6/6 | 5/6 | 5/5 |
| 4 | 1/3 | 3/4 | 3/5 | 6/6 | 4/3 | 6/0 |
| 5 | 5/4 | 6/5 | 5/6 | 6/6 | 6/6 | 6/6 |
| 7 | 3/3 | 4/4 | 3/4 | 6/6 | 6/6 | 6/6 |
| 8 | 6/4 | 0/3 | 0/0 | 6/6 | 6/6 | 6/5 |

EXAMPLE 10

Preparation of 2-Perfluoroalkylethyltris(polyoxyethyleneglycolmonomethylether)silane 2-Perfluoroalkylethyltrichlorosilane, 200 g., 0.30 mole, was dissolved in toluene at 25° C. Polyethyleneglycolmonomethylether having an average molecular weight of 350, 315 g, 0.90 moles, was added slowly to this solution. When the addition was complete, the temperature was raised slowly to 100° C. and held for 24 hours. The solvent was then removed under vacuum leaving a clear viscous liquid.

EXAMPLE 11

Emulsion Preparation:

The product of Example 10 was emulsified in water without added emulsifiers. This emulsion remained clear and colorless for about 1 week. After that time insoluble oligomers formed and precipitated from the emulsion, showing the instability of the aqueous emulsion in the absence of an emulsifier of this invention.

An aqueous emulsion that was stable for more than 2 months was prepared by the method of Example 5, using 2.0 g of the silane and 0.84 g of ("ZONYL" FSK, DUPont Co.) and 97.2 g water. This emulsion was evaluated by the AATCC Test Method of Example 9 and found to give an oil/water repellency ratings on wood of 4/3, and on plate glass of 6/6.

EXAMPLE 12

Repellency Test On Fabrics:

The anionic aqueous emulsion of Example 2 was applied to various fabrics from a bath containing 0.5% of the fluorocarbon silane. The fabrics were dried for 3 minutes at 300° F. The repellency, initially and after one dry cleaning of the fabrics, was determined by the AATCC Test Method 118-1978 where a rating of 6 indicated the highest level of repellency, and compared with the repellency of untreated fabrics. The results are given in Table II.

TABLE II

REPELLENCY PERFORMANCE ON FABRICS
Oil/Water Repellency Rating

| Example | Cotton Init. | Cotton DC | Poly/cotton Init. | Poly/cotton DC | Nylon Init. | Nylon DC |
|---|---|---|---|---|---|---|
| Control(a) | 0/0 | 0/0 | 0/0 | 0/0 | 0/0 | 0/0 |
| 2(a) | 4/5 | 4/5 | 2/5 | 1/5 | 4/5 | 4/5 |
| 2(b) | 5/5 | 5/5 | 4/5 | 4/5 | — | — |

(a) = Without other bath additives.
(b) = With a standard durabilizing finish resin in the bath.
Init = Initial repellency
DC = After one dry cleaning

EXAMPLE 13

Water Hold-Out Test:

The emulsions of Examples 3 and 5, containing 0.5 weight % of the hydrolyzable fluorocarbon silanes, were applied to masonry bricks and tested for water hold-out according to the procedure of Federal Test Method SS-W-110c. A value for the water absorption of less than 1% weight gain is required to pass this standard test. The emulsion of Example 3 showed a 0.1% weight gain, and the emulsion of Example 5, a 0.2% weight gain. These results demonstrate the excellent water repellency and hold-out achieved by emulsions of this invention.

Having thus described and exemplified the invention with a certain degree of particularity, it should be appreciated that the following claims are not to be so limited but are to be afforded a scope commensurate with the wording of each element of the claim and equivalents thereof.

I claim:

1. A reactive aqueous emulsion comprising: (a) an alkoxysilane compound emulsified in water; wherein said alkoxysilane compound is a fluorocarbon silane represented by the formula:

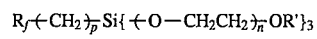

$$R_f\!-\!(CH_2)_p\!-\!Si\{-\!O\!-\!CH_2CH_2)_n\!-\!OR'\}_3$$

wherein $R_f$ is a perfluoroalkyl radical of 3 to 18 carbon atoms; R's are the same or different alkyl radicals of 1 to 3 carbon atoms; p=2 to 4; and n=2 to 10 and (b) an effective amount of an emulsifier of sufficiently high HLB value to simultaneously retain said alkoxysilane compound in a hydrolyzed state and inhibit the resulting hydrolyzed alkoxysilane compound from self-condensation.

2. A reactive aqueous emulsion of claim 1 wherein $R_f$=mixed perfluoroalkyl groups with an average of 8 to 12 carbons.

3. A reactive aqueous emulsion of claim 1 wherein said fluorocarbon silane is perfluoroalkylethyltris(2-(2-methoxyethoxy)ethoxy)silane.

4. A reactive aqueous emulsion of claim 1 wherein said fluorocarbon silane is 2-perfluoroalkylethyltris(2-(2-(2-methoxyethoxy)ethoxy)ethoxy)silane.

5. A reactive aqueous emulsion of claim 1 wherein said fluorocarbon silane is 2-perfluoroalkylethyltris(polyoxyethyleneglycolmonomethylether)silane.

6. A process for coating a substrate comprising the steps of:

(a) emulsifying in water (i) a fluorocarbon silane represented by the formula:

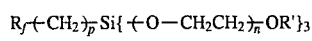

where $R_f$ is a perfluoroalkyl radical of 3 to 18 carbon atoms; R's are the same or different alkyl radicals of 1 to 3 carbon atoms; p=2 to 4; and n=2 to 10 and (ii) an effective amount of an emulsifier of sufficiently high HLB value to simultaneously retain said fluorocarbon silane in a hydrolyzed state and inhibit the resulting fluorocarbon silane from self-condensation thus forming a reactive aqueous emulsion;

(b) allowing said aqueous emulsion of step(a) to hydrolyze forming a reactive aqueous emulsion; and c) contacting a substrate with said reactive aqueous emulsion of step(b).

7. A process for coating a substrate according to claim 6 wherein $R_f$=mixed perfluoroalkyl groups with an average of 8 to 12 carbons.

8. A process for coating a substrate according to claim 6 wherein said fluorocarbon silane is perfluoroalkylethyltris(2-(2-methoxyethoxy)ethoxy)silane.

9. A process for coating a substrate according to claim 6 wherein said fluorocarbon silane is 2-perfluoroalkylethyltris(2-(2-(2-methoxyethoxy)ethoxy)ethoxy)silane.

10. A process for coating a substrate-according to claim 6 wherein said fluorocarbon silane is 2-perfluoroalkylethyltris(polyoxyethyleneglycolmonomethylether)silane.

* * * * *